United States Patent [19]

Hew et al.

[11] Patent Number: 5,545,808
[45] Date of Patent: Aug. 13, 1996

[54] TRANSGENIC SALMONID FISH EXPRESSING EXOGENOUS SALMONID GROWTH HORMONE

[75] Inventors: Choy L. Hew, Thornhill; Garth L. Fletcher, St. John's, both of Canada

[73] Assignees: HSC Research and Development Limited Partnership, Toronto; Seabright Corporation, St. John's, both of Canada

[21] Appl. No.: 212,375

[22] Filed: Mar. 10, 1994

Related U.S. Application Data

[63] Continuation of Ser. No. 669,765, Mar. 15, 1991, abandoned.

[51] Int. Cl.[6] ............................. C12N 5/00; C12N 15/00; C12P 21/06
[52] U.S. Cl. ..................... 800/2; 435/172.3; 435/69.4; 935/63; 800/DIG. 1
[58] Field of Search ............................ 800/2, DIG. 1; 435/172.3, 69.4; 935/63

[56] References Cited

PUBLICATIONS

Vielkind et al., The Induction of a Specific Pigment Cell Type by Total Genomic DNA Injected into the Neural Crest Region of Fish Embryos of the Genus Xiphophorus 1982, pp. 379–389.

Zhu et al., Novel gene transfer into the fertilized eggs of gold fish (*Carassius auratus L.* 1758), 1985.

Sekine et al., Cloning and expression of cDNA for salmon growth hormone in *Escherichia coli*, 1985.

Chen et al., Gene Transfer, Expression and Inheritance of Rainbow Trout and Human Growth Hormone Genes in Carp and Loach, *Transgenic Models in Medicine and Agriculture*, pp. 127–139, 1990, Wiley Liss, Inc.

Hew et al (1988) J. Biol. Chem. 263, 12049–12055.

Idler et al (1989) Gen. Comp. Endocrin. 74, 327–334.

*Primary Examiner*—Jasemine C. Chambers
*Assistant Examiner*—Deborah Crouch
*Attorney, Agent, or Firm*—Townsend and Townsend and Crew

[57] ABSTRACT

An "all fish" chimeric gene construct suitable for gene transfer for commercially important fish comprises the antifreeze gene (AFP) promoter fused to the desired gene sequence which is incorporated into fish embryos. The desired gene sequence is expressed in the transfected fish to provide a transgenic fish having the characteristics of the gene sequence.

7 Claims, 7 Drawing Sheets

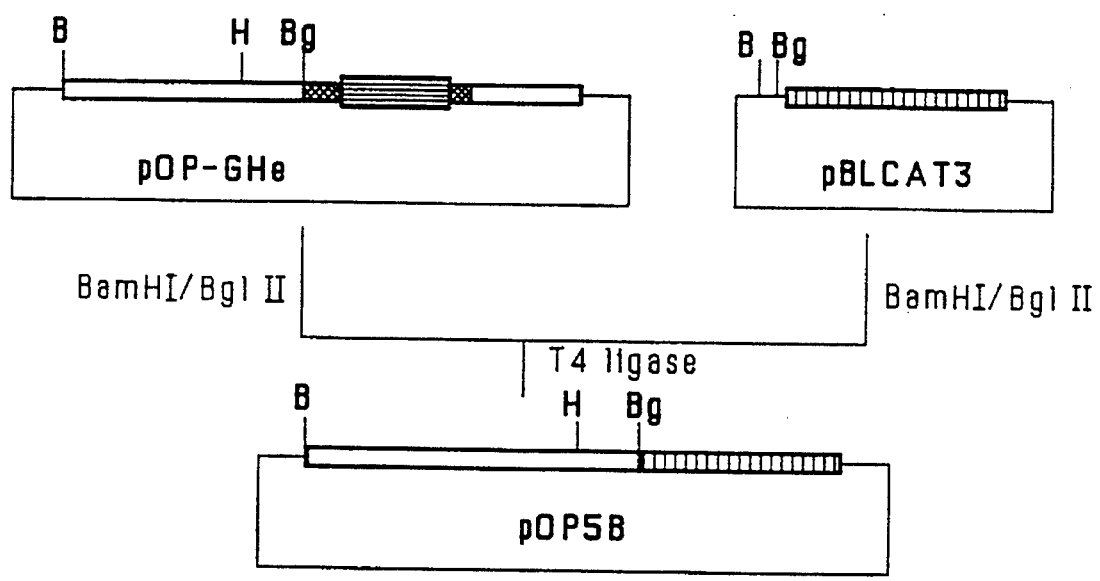
FIG.1.A.

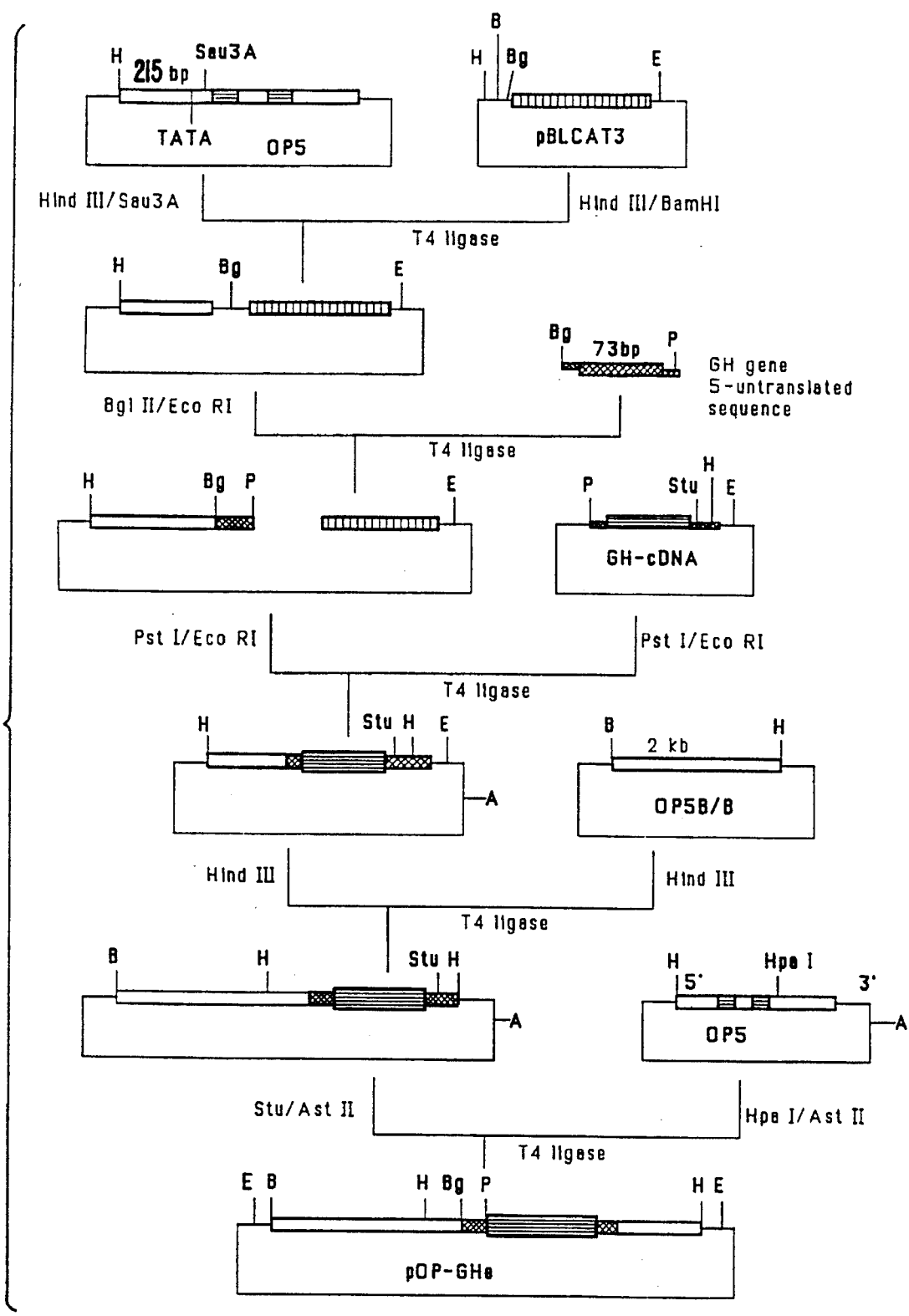
FIG.1.B.

WEIGHT OF TRANSGENIC FISH

WEIGHT OF ONE YEAR OLD TRANSGENIC FISH

| FISH # | 14 | 20 | 28 | 31 | 34 | 42 | NON-TRANSGENIC CONTROLS |
|---|---|---|---|---|---|---|---|
| WEIGHT (g) | 14 | 16 | 65 | 39 | 33 | 6.5 | |
| MAGNITUDE OF INCREASE (FOLD) | 1.8 | 2.1 | 8.6 | 5.1 | 4.3 | 0 | |

TRANSGENIC SALMONID FISH EXPRESSING EXOGENOUS SALMONID GROWTH HORMONE

This is a continuation of application Ser. No. 07/669,765, filed Mar. 15, 1991, now abandoned.

FIELD OF THE INVENTION

This invention relates to transgenic fish and a promoter sequence and 3' non-translated sequence with termination signal particularly useful in developing transgenic fish.

BACKGROUND OF THE INVENTION

Throughout the specification, there are several noted references. The citations for those references are provided below:

Agellon, L. B. and Chen. T. T., (1986) Rainbow trout growth hormone: Molecular cloning of cDNA and expression in E. coli. DNA, 5:463–477.

Cantilo, E. and Regalado, T. G. (1942) Investigaciones realizadas con el extracto anterohysofisario en el desarrollo del Salvelinus fontinalis. Rev. Med. Vet. (Buenos Aires) 24:323–338.

Chen, T. T., Lin, C. M., Zhu, Z., Gonzalez-Villasenor, L. I., Duham, R. A., and Powers, D. A. (1990) Gene transfer, expression and inheritance of rainbow trout and human growth hormone genes in carp and loach. In Transgenic Models in Medicine and Agriculture, 127–139. Wiley-Liss, Inc.

Chen, S. and Evans, G. A. (1990) A simple screening method for transgenic mice using the polymerase chain reaction. Biotechniques, 8:32–33.

Chong, S. S. C., and Vielkind J. R. (1989) Expression and fate of CAT reporter gene microinjected into fertilized medaka (Oryazias latipes) eggs in the form of plasmid DNA, recombinant phage particles and its DNA. Theor. Appl. Genet. 78: 369–380

Davies, L. G., Dibuer, M. D. and Battey, J. F. (1986) Methods in Molecular Biology. Elsevier Science Publishing Co.

Davies, P. L., Fletcher, G. L. and Hew, C. L. (1989) Fish antifreeze protein genes and their use in transgenic studies. in: Oxford Surveys on Eukaryotic Genes, 6: 85–110. Edited by Norman Maclean, Published by Oxford University Press.

Davies, P. L. and Hew, C. L. (1990) Biochemistry of fish antifreeze proteins. The FASEB Journal, 4:2640–2648.

Du, S. J. and Hew, C. L. (unpublished) The isolation and characterization of GH genes from Atlantic salmon and Chinook salmon.

Fletcher, G. L., Shears, M. A., King, M. J., Davies, P. L. and Hew, C. L. (1988) Evidence for antifreeze protein gene transfer in Atlantic salmon (Salmo salar). Can. J. Fisheries and Aquatic Sciences, 45:352–357.

Fletcher, G. L., Idler, D. R., Vaisius, A. and Hew, C. L. (1989) Hormonal regulation of antifreeze protein expression in winter flounder. Fish Physiology and Biochemistry, 7:387–393.

Friedenreich, H. and Schartl, M. (1990) Transint expression directed by homologous and heterologous promoter and enhancer sequences in fish cells. Nucleic Acids Research, 18:3299–3305.

Gill, J. A., Sumpyer, J. P., Donaldson, E. M., Souza, L., Berg, T., Wypych, J. and Langley, K. (1985) Recombinant chicken and bovine growth hormones accelerate growth in aquacultured juvenile Pacific salmon, (Oncorhynchus kisutch). Bio/Technology, 3:643–646.

Gong, Z. Y., Hew, C. L. (unpublished) Functional analysis of fish antifreeze gene promoters: presence of silencers.

Gong, Z. Y., Vielkind, J., Hew, C. L. (unpublished) Functional analysis and temporal expression of fish antifreeze gene promoters in Japanese medaka embryos.

Gong, Z. Y., Fletcher, G. L. and Hew, C. L. (unpublished) Predominantly expression of antifreeze genes in liver.

Guyomard, R., Chourrout, D., Leroux, C., Houdebine, L. M. and Pourrain, F. (1989) Integration and germ line transmission of foreign genes microinjected into fertilized trout eggs. Biochimie, 71:857–863.

Hammer, R. E., Brinster, R. L. and Palmiter, R. D. (1985) Use of gene transfer to increase animal growth. Cold Spring Harbor Symp. Quant. Biol. 50:379–388.

Hanley, T., and Merlie, J. P. (1991) Transgene detection in unpurified mouse tail DNA by polymerase chain reaction. BioTechniques. 10:56—56.

Hew, C. L., Slaughter, D., Joshi, S. B., and Fletcher, G. L. (1984) Antifreeze polypeptides from the Newfoundland ocean pout, Macrozoarces americanus: Presence of multiple and compositionally diverse components. J. Comparative Physiology B, 155:81–88.

Hew, C. L., Wang, N. C., Joshi, S., Scott, G. K., Hayes, P. H., Buettner, B. and Davies, P. L. (1988) Multiple genes provide the basis for antifreeze protein diversity and dosage in the Ocean Pout (Macrozoares americanus). J. Biol. Chem., 263:12049–12055

Hew, C. L., Trinh, K. Y., Du, S. J., and Song, S. D. (1989) Molecular cloning and expression of salmon pituitary hormones. Fish Physiology and Biochemistry, 7:375–380.

Hoar, W. S. (1988) The physiology of smolting salmonids. in Fish Physiology, vol. 11:275–343. edited by Hoar, W. S. and Randall, D. J. Academic Press.

Kawauchi, H. Moriyama, S., Yasuda, A., Yamaguchi, K. Shirahata, K., Kubota, J. and Hirano, T. (1986) Isolation and characterization of Chum salmon growth hormone. Archives of Biochemistry and Biophysics, 244:542–552.

Li, X., Trinh, K., Hew, C. L. Buettner, B., Baenziger, J. and Davies, P. L. (1985) J. Biol. Chem. 260:12904–12909.

Liu, Z., Moav, B., Faras, A. J., Guise, K. S., Kapuscinski, A. R. and Hackett, P. B. (1990) Development of expression vectors for transgenic fish. Bio/Technology 8:1268–1272.

Luchow, B., and Schutz, G. (1987) CAT construction with multiple unique restriction sites for the functional analysis of eucaryotic promoters and regulatory elements. Nucleic Acid Res., 15:5490.

McHale, R. H., Stapleton, P. M., and Bergquist, P. L. (1991) Rapid preparation of blood and tissue samples for polymerase chain reaction. BioTechniques. 10:20–22.

Palmiter, R. D., Brinster, R. L., Hammer, R. E., Trumbauer, M. E., Rosenfeld, M. G., Birnberg, N. C. and Evans, R. M. (1982) Dramatic growth of mice that develop from eggs microinjected with metallothionein-growth hormone fusion genes. Nature, 300:611–615.

Rokkones, E., Alestrom, P., Skjervold, H. and Gautvik, K. M. (1989) Microinjection and expression of a mouse metallothionein human growth hormone fusion gene in fertilized salmonid eggs. J. Comp. Physiol. B., 158:751–785.

Sekine, S., Mizukami, T., Nishi, T., Kuwana, Y., Saito, A., Sato, M., Seiga, I., and Kawauchi, H. (1985) Cloning and expression of cDNA for salmon growth hormone in E. coli. Proc. Natl. Acad. Sci. U. S. A., 82:4306–4310.

Tuckmann, H. (1936) Action de lhypophyse sur la morphogenese et la differentiation sexuelle de Girardinus guppii. C. R. Soc. Biol. 122:161–164.

Vielkind, J., Haas-Andela, H., Vielkind, U. and Anders, F. (1982) The induction of a specific pigment cell type by total genomic DNA injected into the neural crest region of fish embryos of genus (Xiphophorus). Mol. Gen. Genet. 185: 379–389.

Vize, P. D., Michalska, A. E., Ashman, R., LLoyd, B., Stone, B. A., Quinn, P., Wells, J. R. E. and Seamark, R. F. (1988) Introduction of a porcine growth hormone fusion gene into transgenic pigs promotes growth. J. Cell Science, 90: 295–300.

Zafarullah, M., Ronham, K. and Gedamu, L. (1988) Structure of the rainbow trout metallothionein @gene and characterization of its metal-responsive region. Mol. Cell Biol., 8:4469–4476.

Zhang, P., Hayat, M., Joyce, C., Gonzalez-villasenor, L. J., Lin, C. M., Dunham, R. and Chen, T. T. and Powers, D. A. (1990) Gene transfer, expression and inheritance of pRSV-rainbow trout GH-cDNA in the common carp, Cyprinus carpio (Linnaeus). Molecular Reproduction and Development, 25:3–13.

Zhu, Z., Liu., G., He, L. and Chen, S. (1985) Novel gene transfer into fertilized eggs of goldfish (Carassius auratus L. 1785). Z. Angew. Ichthylo., 1:31–34.

Zhu, Z., Xu, K., Li, G., Xie, Y. and He, L. (1986) Biological effects of human growth hormone gene microinjected into the fertilized eggs of loach (Misgurnus anguillicaudatus). Kexue Tongbao, 31:988–990.

A variety of attempts and successes have been made to develop transgenic fish and other animals. Growth hormone has been of particular interest. Growth hormone is a single chain polypeptide hormone that plays a principal role in the regulation of somatic growth and development in animals. Many approaches have been made to increase fish growth by growth hormone. These include the feeding of pituitary extracts (Tucker 1936, Cantilo and Regalado 1940), injection or implantation of purified recombinant-derived growth hormone (Gill et al. 1985, Sekine et al. 1985, Kawauchi et al. 1986, Agellon et al. 1988). All these results clearly showed that growth hormone alone is effective in stimulating fish growth. However, all these studies have limited application in aquaculture, and one major drawback is that the phenotype can not be inherited.

Gene transfer technique has become a new and powerful approach to manipulate the genetic and phenotypic characteristic of both animals and plants. Various reports have been made in the production of transgenic fish. The first transgenic study on fish was reported by Vielkind et al. (1982). These investigators injected swordtail tumour genes into the Platyfish, and found that the injected swordtail Tu genes could induce T-melanophore induction in Tu-free Platyfish. In 1985 and 1986, Zhu et al. reported the production of transgenic fish by growth hormone gene transfer. Using a mouse metallothionein promoter ligated to a human GH structural gene, they successfully produced transgenic loach, goldfish and silver carp. On the average, the transgenic fish was 1 to 3 times larger than control. Since then, several reports using similar gene constructs have been published (Rokkones et al. 1989, Guyomarde et al. 1989, Chen et al. 1990)

Most, if not all of these studies were carried out by using either mammalian GH or mammalian gene and viral promoters. To be acceptable in aquaculture, the promoter(s) and gene(s) used in transgenic fish should be derived preferably from fish protein genes without posing any potential health hazards. Furthermore the production of a strain of faster growing fish in an economically important species such as salmonids with an all fish gene construct will be beneficial to fish farming.

We have discovered the successful production of transgenic Atlantic salmon by using a fish gene promoter derived from ocean pout antifreeze gene (OP-AFP), (Hew et al. 1988) and the GH cDNA gene from chinook salmon (Hew et al. 1989).

According to an aspect of the invention, a promoter for use in constructing a chimeric gene construct is provided. The promoter comprises an antifreeze gene (AFP) promoter having characteristics functionally corresponding to the AFP promoter derived from Ocean pout and 3' sequence containing the normal RNA transcriptional termination signal. The promoter is characterized by a 2 kb Bam H1 - B1 II fragment of Op-AFP of FIGS. 1a and 1b and Table I. The 3' sequence is characterized by the 1 kb HpaI - Hind III fragment in FIG. 1b. Functional analysis of other antifreeze promoters, including wolffish (WO), sea raven (SR) and winter flounder (WF), shows that they can be used in a similar fashion (Table II). Here only the Ocean pout antifreeze protein promoter is used as a teaching example in producing transgenic fish.

The invention provides specific embodiments, such as the analysis of transient expression of the OP-AFP gene promoter activities in a salmonid cell line and the Japanese medaka embryos, the construction of AFP-GH fusion gene, and its gene transfer by microinjection, screening of transgenic salmon by polymerase chain reaction (PCR), size and growth rate measurements.

BRIEF DESCRIPTION OF THE DRAWINGS

FIGS. 1A–B A. Construction of pOP-CAT for transient CAT assay in salmonid cell lines and Japanese medaka embryos. B. Construction of all fish chimeric gene (pOP-GHe) for gene transfer;

DETAILED DESCRIPTION OF THE PREFERRED EMBODIMENTS

Figure 2:
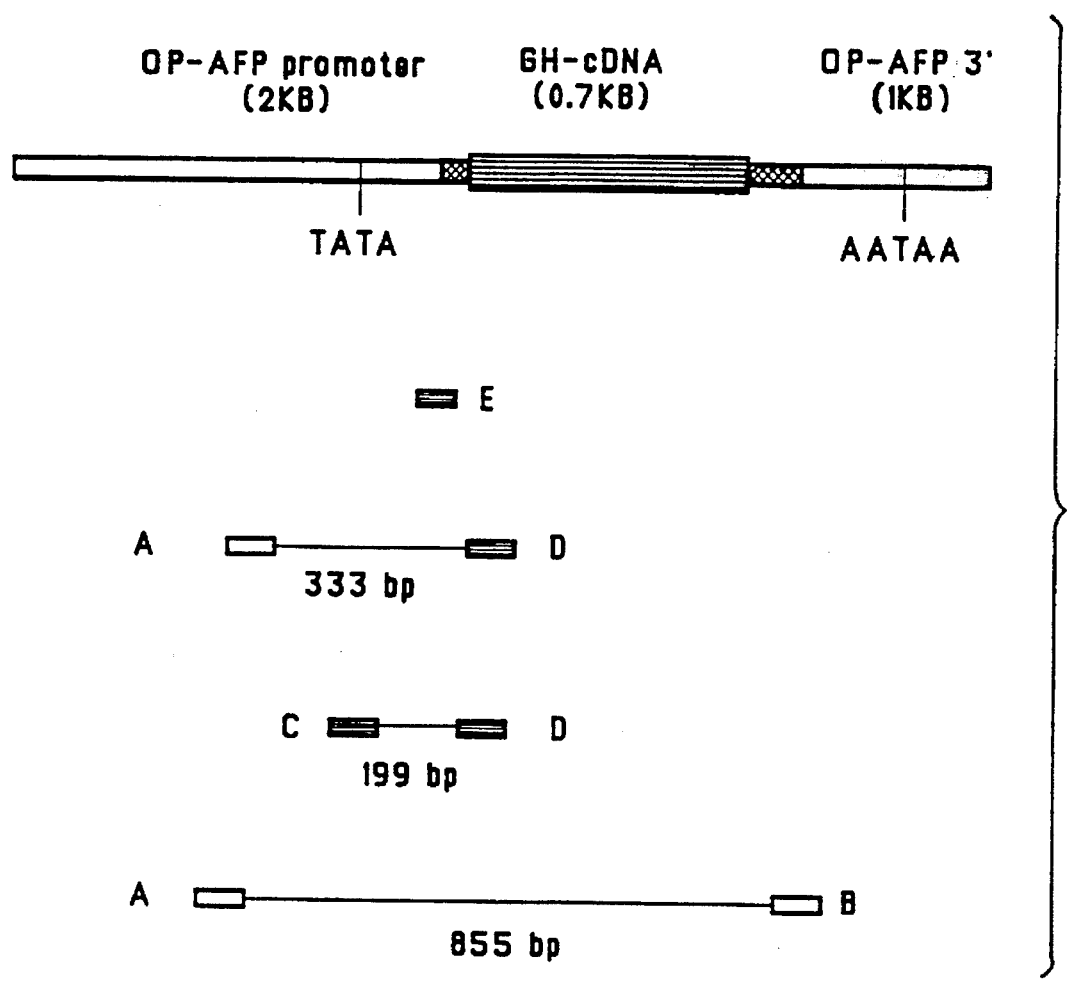
FIG. 2. Strategy of PCR analysis. Three sets of primers were used to detect the presence of transgene. The distance between primers are 813 bp for primer A and B, 335 bp for primers A and D, 119 bp for primers C and D.

The present invention provides the successful production of transgenic fish with dramatic expression of the desired genetic trait. A chimeric gene, pOP-GHe was constructed by using antifreeze promoter linked to the chinook salmon GH cDNA clone. This gene construct pOP-GHe was microinjected into fertilized, nonactivated Atlantic salmon eggs via the micropyles, in accordance with the technique described in applicants' co-pending U.S. application Ser. No. 278,463 filed Dec. 1, 1988 and the subject matter of which is hereby incorporated by reference. Transgenic Atlantic salmon carrying the transgene were generated with an incorporation frequency of at least 2%. The presence of transgene was detected by polymerase chain reaction using specific oligonucleotide primers. These transgenic fish showed dramatic increase in their weight and growth rate. At eight months old, the average increase of the transgenic fish was 4-fold and the largest transgenic fish was eight times bigger than the non-transgenic controls. These studies demonstrated that the AFP promoter was effective in producing large transgenic salmon and would be applicable to many different species of fish. Use of fish growth hormone with promoter of this invention will result in transgenic fish up to eight times larger than controls. This is the largest increase that has been reported to date for a transgenic fish. Comparing with the 2-fold increase in transgenic mouse (Palmiter et al. 1982) and transgenic pig (Vize et al. 1988), these studies indicate that growth of transgenic salmon is more pronounced.

The data later presented in this specification demonstrate the successful production of transgenic salmon by using a DNA construct derived from fish genes. Several earlier GH gene transfer studies on fish were made by using mammalian metallothionein promoters or viral promoters and human or rat GH genes. (Zhu et al. 1986, Rokkones et al. 1989, Guyomard et al. 1989 and Chen et al 1990). There are two problems associated with using those heterologous gene constructs. First, the transgenic fish produced using mammalian GH genes may not be suitable or acceptable for human consumption. Secondly, it has been reported by Friedenreich and Schartl (1990) that the mammalian GH gene could not be spliced sufficiently in fish cell line in vitro, and they could not detect the expression of the GH gene in fish cells. This may explain why Rokkones et al. (1989) and Guyomard et al (1989) could not observe faster growth in their transgenic fish by using mammalian metallothionein-mammalian GH fusions or viral promoter-mammalian GH genes. Zhang et al. (1990) and Chen et al. (1990) used the rainbow trout GH gene for gene transfer in Carp and Loach, using the retrovirus promoter. However, the transgenic fish in those investigations were only 20% larger than the controls, and the trout GH gene used lacted the signal sequence needed for the proper secretion of GH.

In our development of the invention, Ocean pout antifreeze gene promoter and transcription termination signal were ligated with chinook salmon GH gene, both of which are derived from fish genes, therefore avoiding the problems associated with the use of mammalian or vival genes for gene transfer in commercially important fish.

The Ocean pout AFP is a member of the type 3 AFP (Davies and Hew 1990). It has approximately 150 gene copies (Hew et al. 1988, Davies et al. 1989). The protein and genomic structure of this AFP have been well characterized by us (Hew et al. 1984, 1988, Li et al. 1985, 1989). More recently, its promoter sequences have been investigated in both the salmonid cell lines and the Japanese medaka embryos (Gong and Hew unpublished, Gong et al. unpublished. See Table II). The Ocean pout AFP gene is expressed predominantly in liver cells (Gong et al. unpublished), all of these manuscripts being incorporated herein by reference.

Unlike the type 1, alanine-rich AFP from the winter flounder which is synthesized only in the winter, the Ocean pout AFP is present all year around, albeit at a higher concentration during the winter months (Fletcher et al. 1989). The following data demonstrate that the OP-AFP promoter is a very effective promoter for inducing GH gene or other desired compatible gene expression in fish, such as Atlantic salmon. Although there is no antifreeze gene in salmonids, it is likely that the transcriptional factors controlling the OP-AFP gene expression exist in salmon. This is consistent with our earlier investigation in producing transgenic Atlantic salmon using the type I antifreeze protein gene from the winter flounder (Fletcher et al. 1988). In that investigation, a DNA coding for the genomic sequence of the AFP gene and its 5' and 3' flanking sequences were used. Transgenic founder animals and F1 generations producing circulating AFP in the serum were achieved (Shears et al. manuscript in preparation). Our studies of the ocean pout promoter in the salmonid cell lines, the Japanese medaka embryos and the positive results from the transgenic Atlantic salmon indicate that the promoter is useful in a variety of fish species. The present AFP gene construct can be further developed into a gene cassette where many other fish genes of interest can be inserted. The Ocean pout antifreeze gene is expressed predominantly in liver, a tissue well suited for the production of secretory proteins. Furthermore, the AFP gene is present only in small number of fish species. Its detection to demonstrate fish transgenic properties, as exemplified in the following, is simple with minimum contribution from the host DNA.

EXPERIMENTAL PROCEDURES

Atlantic salmon eggs collection

Mature Atlantic salmon (*Salmo salar*) were captured 2–3 weeks prior to spawning from the exploits and Colinet river systems, Newfoundland, and transported live to the Ocean Sciences Centre, Memorial University of Newfoundland. The fish were maintained at seasonally ambient photoperiod in 2×2×0.5 m aquaria supplied with freshwater and air.

Eggs and sperms were stripped from salmon which had been anaesthetized in a dilute solution of t-amyl alcohol. Eggs were kept in 4° C., and were fertilized up to 2h prior to microinjection and rinsed with several changes of ice-cold salmon Ringer solution. Activation occurred when the eggs were placed in fresh water after microinjection (Fletcher et al. 1988).

Medaka egg collection

Japanese medaka (*Oryzias latipes*) were maintained at Dr. J. Vielkind's laboratory, cancer research centre, Vancouver. The reproductive activities of the adults were induced with artificial photoperiod of 10 hours darkness to 14 hours light. Fertilized eggs attached to females were collected 1–2 h after the onset of light and maintained in Ringer solution (0.75% NaCL, 0.02% KCL, 0.02% $CaC_2L$:, pH 7.3) at 12° C. prior to injection. Injected medaka embryos were reared in medium containing 0.1% NaCL, 0.003% KCL, 0,004% $CaCL_2$·$H_2O$, 0.016% $MgSO_4$·$7H_2O$, 0.0001% methylene blue and transferred to aquarium water immediately after hatching (Chong and Vielkind 1989).

PLASMID CONSTRUCTION a. Ocean pout antifreeze promoter-CAT fusion gene (pOP-CAT).

The 2 kb Bam H1-Bgl II fragment containing the OP-AFP promoter was subcloned into plasmid pBLCAT3 (Luckow and Schutz 1987) at Bam HI, Bgl II sites to form OP-CAT fusion gene (FIG. 1A). Supercoil plasmids for transfection were prepared by ethidium bromide CsCL gradient centrifugation. The 2 kb Bam H1 - Bgl II fragment is isolated from the gene sequence of the Ocean pout AFP gene as described in Hew et al (1988). The restriction map of plasmid Op5 is shown in Table 1. The construction and promoter activities of other antifreeze are also included in Table II.

b. Ocean pout antifreeze promoter-salmon growth hormone fusion gene (pOP-GHe).

The -215- bp Hind III-Sau 3A fragment (SEQ ID NO.4) from plasmid OP5 containing the OP-AFP promoter (Hew et al. 1988) of Table I, was subcloned into plasmid pBLCAT3 in pUC 18 (Luckow and Schutz 1987) at Hind III, Bam HI sites as illustrated in FIG. 1B. The plasmid was digested with Blg II, and then ligated with a 73 bp Bgl II-Pst I synthetic linker which contains the 5'-untranslated sequence of chinook salmon GH gene (Du and Hew unpublished). The GH gene has been characterized in Hew et al (1989) and is specifically outlined in the salmon growth hormone (SEQ ID NO.1). The ligated DNA was digested with Pst I and Eco RI, and the larger fragment containing the OP-AFP promoter, chinook salmon GH 5'-untranslated sequences and pUC 18 sequence was purified by gel elution. This larger fragment was then ligated with a 709 bp Pst I-Eco RI fragment containing chinook salmon GH coding sequence and part of 5' and 3'-untranslated region (Hew et el. 1989). The resultant plasmid was cut with Hind III and cloned into a plasmid which contained the 2kb Bam H1-Hind III (SEQ ID NO.5) flanking sequence from the ocean pout antifreeze gene promoter (Hew et al. 1988). This plasmid was then digested with Stu I and Aat II, and the larger fragment which contained the OP-AFP promoter and GH coding region and part of the GH 3'-untranslated sequence, was then ligated to a 1 kb Hpa I-Aat II fragment from OP5 plasmid which included the OP- AFP gene polyadenylation and the transcription termination signals (Hew et al. 1988). The final construct was designated as pOP-GHe (FIG. 1B).

TRANSIENT CAT ASSAY IN SALMON CELL LINES

RTH-149, a rainbow trout hepatoma cell line was kindly provided by Dr. L. Gedamu. The cells were maintained at 18° C. in minimus essential medium supplemented with 25 mM HEPES buffer (Gibco). The fish cells were transfected with DNA by calcium phosphate co-precipitation with glycerol shock and CAT assay were carried out essentially according to Davies et al. (1986) and modified for fish cells by Zafarullah et al. (1988).

TRANSIENT CAT ASSAY IN JAPANESE MEDAKA.

The Supercoiled pOP-CAT plasmid DNA (approximately 500 pl, 10s copies) was microinjected into the cytoplasm of the fertilized medaka eggs prior to or immediately after cleavage. Phenol red was added to the DNA to a final concentration of 0.25% to aid in visualization of injection. CAT assays were performed according to Chong and Vielkind (1989). For 5 day embryos, batches of five embryos were used for CAT assay. For hatched fish, individual fry was used for CAT assay.

GENE TRANSFER IN Atlantic SALMON BY MICROINJECTION.

The 4kb insert in pOP-GHe was excised by Eco RI digestion and dissolved in saline buffer at a concentration of 3 µg/ml. Approximately (2–3 nl, $10^6$ copy) of the DNA insert was injected through the micropyle into a fertilized, nonactivated salmon egg cytoplasm (Fletcher et al. 1988) in accordance with the procedure of the aforementioned U.S. patent application Ser. No. 278,463. Approximately 500 eggs were injected. The survival rate was 80% as compared to the noninjected control.

SYNTHESIS OF OLIGONUCLEOTIDE PRIMERS FOR PCR

For PCR analysis, four primers were synthesized by the Biotech Service Centre, Hospital for Sick Children, Toronto, Canada. As shown in FIG. 2, primer A, located at position +27 to +47 relative to the TATA box, is from the sense strand of the OP-AFP gene promoter; Primer B, located at position +861 to +881 relative to the TATA box, is from the antisense strand of the OP-AFP gene 3, flanking region. Primer C, located at position +161 to +181, is from the sense strand of GH coding sequence; While primer D, located at position +339 to +359, is from the antisense strand of GH gene.

Primer A 5'-GTCAGAAGTCTCAGCTACAGC-3'(SEQ ID NO.6)

Primer B 5'-ATCTCAACAGTCTCCACAGGT-3'(SEQ ID NO.7)

Primer C 5'-TCTGCTGATGCCAGTCTTACT-3'(SEQ ID NO.8)

Primer D 5'-ACAGAAGTCCAGCAGGAATAT-3'(SEQ ID NO.9)

DNA ISOLATION FROM BLOOD CELLS FOR PCR

Thirty microliters of blood was collected from one year old fish. One microliter of the blood was lysed in 50 µl of 10 mM NaOH, boiled in water bath for 3 min, then centrifuged for 3 min. Two microliters of the supernatant were used for PCR directly.

PCR AMPLIFICATION

PCR was carried out in 70 µl reaction solution containing 50 mM KCL, 10 mM Tris, 2.5 mM MgCL:, 1 µM of each primer, four deoxyribonucleotide triphosphate at 200 µM each, and 2.5 units of Taq DNA polymerase (Promega), 100 µl of mineral oil was added to prevent condensation. Amplification was started by denaturating the DNA at 92° C. for 3 min, followed by 30 PCR cycles. Each cycle included 1 min at 92° C. (denaturation), 1 min at 60° C. (annealing), and 2 min at 72° C. (extension). After the final cycle, the reaction was held for another 10 min at 72° C. in order to complete all the reaction. PCR was carried out by using the PTC-100 Programmable Thermal Controller (MJ Research, Inc. Ocala, Fla.).

ANALYSIS OF THE PCR PRODUCT BY AGAROSE GEL ELECTROPHORESIS AND SOUTHERN BLOT

Twenty microliters of the amplified product was subjected to electrophoresis on a 0.8% agarose gel, and the DNA products were visualized by ethidium bromide staining. The DNA was transferred to a Nylon membrane (Amersham) for Southern analysis. A 17 bp GH specific oligonucleotide probe E, 5'-GAAAATGTTCAATGACT-3'(SEQ ID NO.10), from sequence of chinook salmon GH cDNA sense strand (+277 to +294) (FIG. 2) was end labelled with $p^{32}$ by T4 kinase and used as probe for Southern blot.

TEST RESULTS OF THE ABOVE PROCEDURES

1. Ocean pout AFP promoter can function in salmonid cells in vitro.

Figure 3:
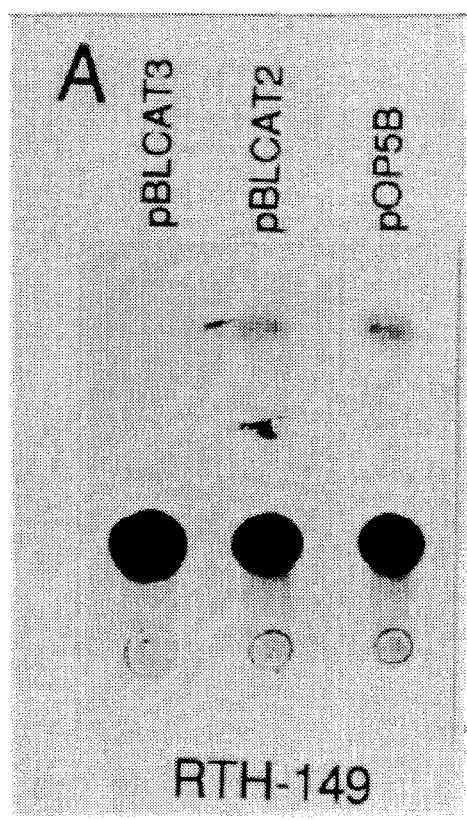
FIG. 3. Analysis of the OP-AFP promoter activity in rainbow trout hepatoma cells by CAT assay.

To test the effectiveness of the OP-AFP promoter, the OP-CAT construct was transfected into RTH 149 cell line for CAT assay. As showed in FIG. 3, CAT activity was clearly detected. The level of CAT activity resulted from OP-CAT was comparable to that from pBLCAT2, which has the thymidine kinase promoter from Herpes simplex virus; however, when these cells transfected with pBLCAT3, a promoterless CAT construct, little or no CAT activity was detected. Similar results were obtained with Chinook salmon embryonic cells (CHSE-124) and Chum salmon heart cells (CHH-1). These results suggest that OP-AFP promoter can be used to target the GH gene expression in salmonids. Although the salmonids including the rainbow trout lack the AFP gene, these cells contain all the transcription factors required for the expression of the AFP gene.

2. Ocean pout AFP promoter can function in Japanese Medaka in vivo.

Figure 4:
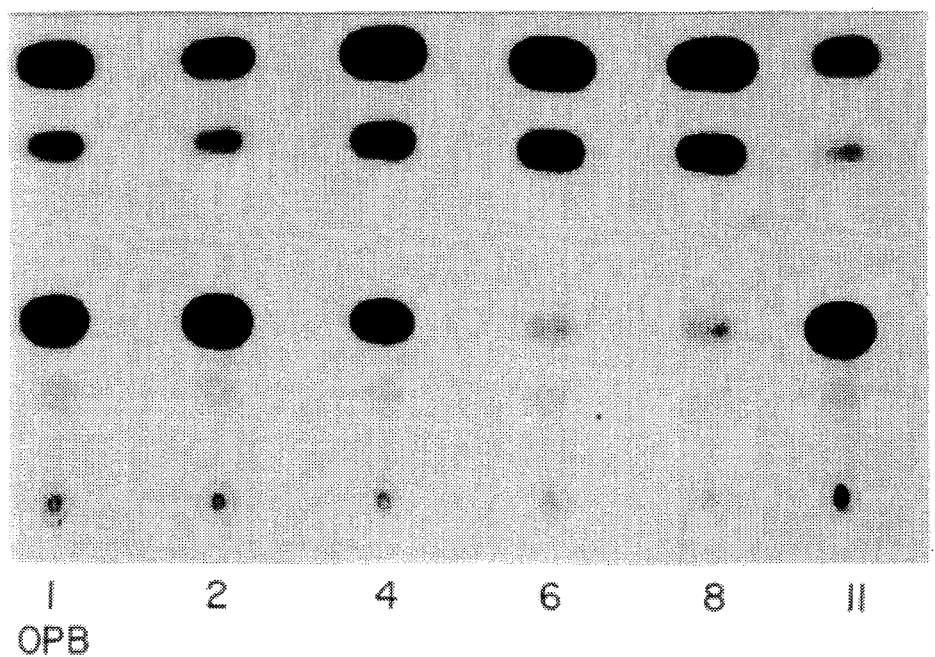
FIG. 4. Time course analysis of CAT expression in embryos injected with OP-CAT. A pool of five embryos were used for CAT assay of 2 days, 4 days and 7 days embryos. Individual larval was used for the CAT assay of hatched medaka (one day after hatching). Embryos injected with pBLCAT3 was used as negative control.

To further investigate the suitability of the OP-AFP promoter in gene transfer, the OP-CAT construct was microinjected into medaka eggs. CAT activity was determined from embryos at different times during development. As showed in FIG. 4, the CAT activity was first detected at 48 hours after the injection, the activity reached the maximum at 6–7 days, then the CAT activity began to decline. However the CAT activity was still detectable even in the hatched fish (11–12 days). In contrast, the CAT activity was not detected in the uninjected embryo or embryo injected with pBL-CAT3. This result confirms that the OP-AFP promoter is active in a variety of fish species.

3. The PCR-based screening strategy.

To screen for the presence of transgenic salmon, three different sets of primers were used, Primers A/D, primers C/D and primers A/B (FIG. 2). The basis for using primer A/B is that the sequences of primer A and Primer B are specific for OP-AFP, which are absent in Atlantic salmon, therefore DNA from the nontransgenic salmon can not be amplified when using primers A/B for PCR. Only the DNA from the transgenic fish can be amplified by using primer A/B, and will generate a 855 bp DNA fragment by PCR.

The basis of using primers A/D is similar as using primer A/B. Although primer D is derived from chinook salmon GH cDNA, and might hybridize with the endogenous Atlantic salmon GH gene, primer A is specific for the OP-AFP gene. Hence the DNA from nontransgenic fish can not be amplified by using primers A/D, only the DNA from transgenic fish can be amplified and generate a 333 bp DNA fragment.

The basis for using primers C/D is different from that of other two sets. The sequences for both primer C and D are from the chinook salmon GH cDNA, which could hybridize with the Atlantic salmon GH gene, and therefore DNA from Atlantic salmon can be amplified by using primer C/D. However there is an intron (intron 2) between primer C and primer D, the distance between primer C and primer D is 344 bp (Du and Hew unpublished). Primers C/D will generate a 344 bp fragment in all the DNA samples. The transgene pOP-GHe was constructed using chinook salmon GH cDNA which lacks the intron and the distance between primer C and primer D is 199 bp. Primers C/D will generate two fragments in transgenic salmon, a 344 bp from the endogenous GH gene and a 199 bp from the GH cDNA insert.

4. The identification of transgenic salmon by PCR.

Preliminary analysis of the DNA extracted from 100 one month old salmon embryos revealed that two of them (2%) contained the injected sequence (pOP-GHe).

Eight months after hatching, the salmon were large enough to tag for identification. At this time, 50 of the 459 salmon in the aquaria were weighed and blood sampled for PCR analyses. These 50 included the 14 largest salmon the aquaria (>8 gm body weight) and 26 additional fish with body weights ranging from 5 to 14 gm.

The PCT analysis was carried out without the analyst knowing the size of any of the fish. In other words, the analysis was carried out "blind" in order to be certain to eliminate any bias by the analyst.

Figure 5A:
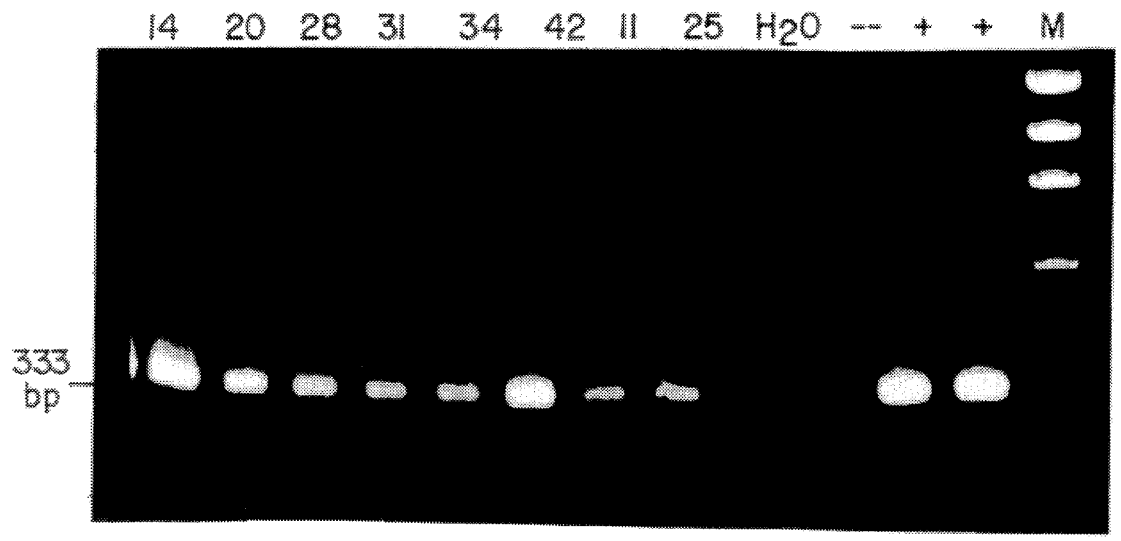
FIGS. 5A–B. Screening of transgenic salmon by PCR using primers A/B. a. Analysis of PCR amplified products by agarose gel electrophoresis, b. Southern blot analysis of the PCR product by using GH specific probe E.

Eight month old Atlantic salmon developed from the eggs injected in November 1989 with pOP-GHe were bled in October 1990. The DNA from the nucleated blood cells were used directly for PCR analysis using primer A/D to determine the presence of the pOP-GHe transgene. Out of 50 fish analyzed, eight were shown to be positive. As showed in FIG. 5A, a 333 bp fragment was generated from salmon #14, #20, #28, #31, #34, #42, #11, #25 and the positive control (pOP-GHe), in contrast this 333 bp fragment was absent in the noninjected salmon. The size of the amplified fragment (333 bp) corresponded with the size predicted from the transgene sequence.

Figure 5B:
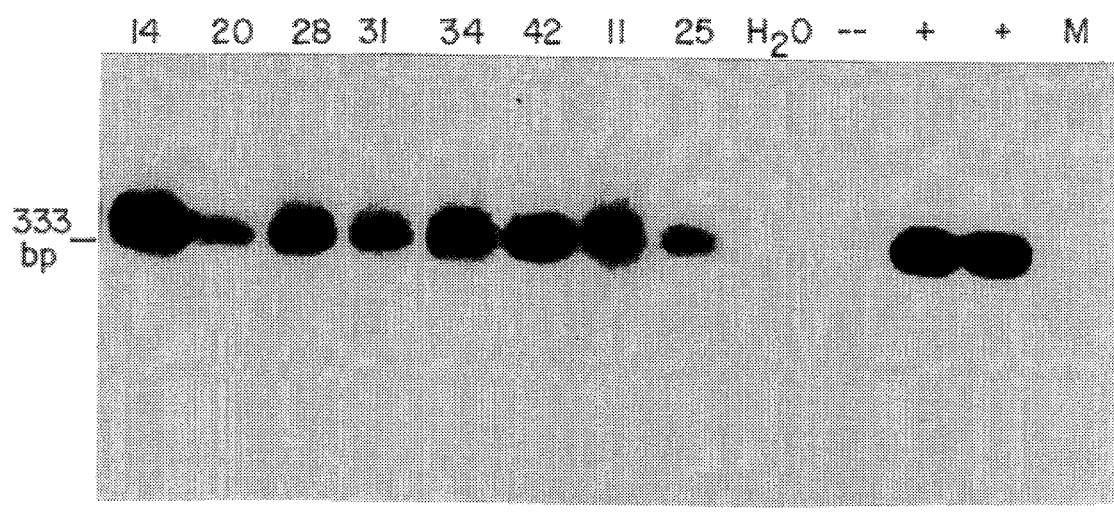
Figure 6:
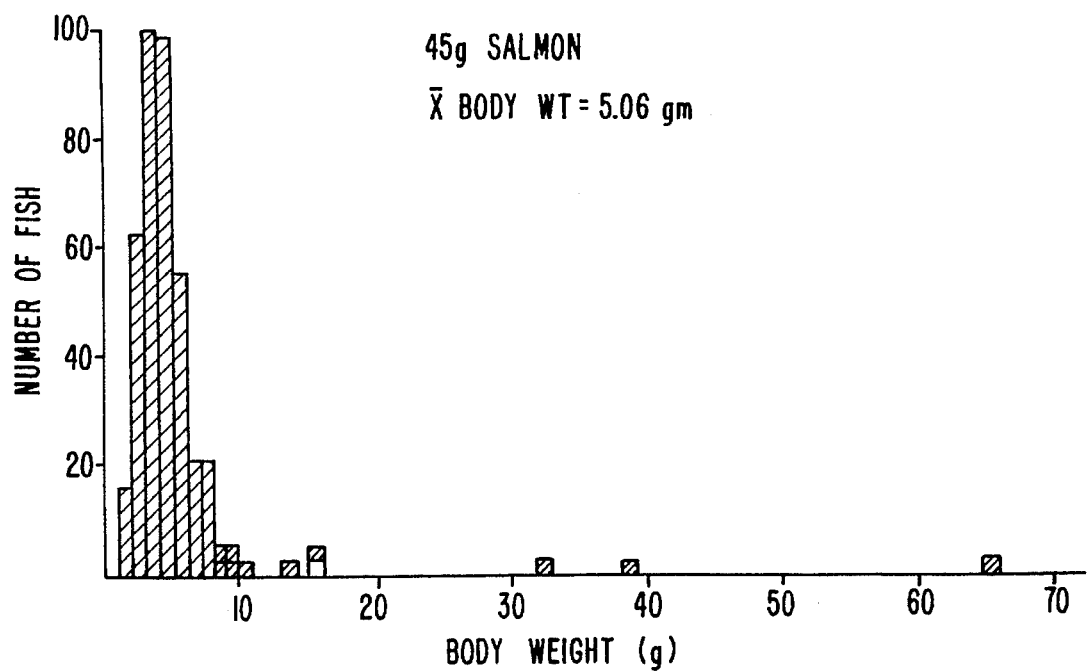
FIG. 6. The size distribution of transgenic salmon and nontransgenic salmon.

To confirm that the amplified 333 bp DNA fragment was derived from the transgene pOP-GHe, the DNA was transferred to a nylon membrane for Southern blot hybridized with a GH specific probe E (FIG. 2) which was from the sequence between the primer A and primer D, and the result showed that all the 333 bp hybridized with the probe E (FIG. 5B). This confirmed that the 333 bp DNA fragment was in fact derived from the transgene pOP-GHe.

To further confirm that the presence of transgene pOP-GHe in the positives, the DNA were amplified by using primers C/D. As discussed in the screening strategy, the expected 344 bp DNA fragment derived from the endogenous Atlantic salmon GH gene were found in all the salmon analyzed. An additional smaller DNA fragment (199 bp) were found from fish #14, #20, #28, #31, #34 and #42, #11 and #25. This 119 bp fragment was derived from the chinook salmon GH transgene. These positives were the same ones as obtained by using primers A/D, thus confirming that fish #14, #20, #28, #31, #34, #42, #11 and #25 were transgenic salmons.

5. The GH coding regions of the transgenes are intact in the transgenic salmon.

To determine the integrity of the GH coding sequence of the transgene, primers A/B were used for PCR analysis. Primers A and primer B were derived from the sequences of the OP-AFP gene 5' and 3', which were located outside of the 5' and 3' of the GH coding sequence in the transgene (FIG. 2), therefore, if the GH coding in the transgene was intact in the transgenic fish, a 855 bp DNA fragment should be generated when using primers A/B to amplify the DNA from the transgenic fish. A 855 bp fragment was found in all the eight positives, indicating that the GH transgene was intact in the transgenic salmon.

6. The growth performance of the transgenic fish.

a. Weight of the transgenic fish

Of six salmon found to be transgenic for the growth hormone gene construct, five of them were amongst the six largest fish in the aquarium. The chances of the observation occurring by coincidence are exceedingly low. The average weight of the six transgenic fish was 29.2±0.3 gm. The average weight of all 459 fish in the aquarium was 5.06±1.0 gm. Thus on average the transgenic fish were four times larger than the non-transgenic controls and approximately six times the average size of the salmon in the aquarium. The largest transgenic fish in the aquarium was eight times larger than the non-transgenic controls and 17 times larger than the average fish in the tank.

b. The growth rate of the transgenic fish

In order to estimate growth rates, the fifty fish that had been blood sampled and tagged were reweighed 100 days later. The mean growth rates of the six transgenic salmon during this period was 0.766±0.18% per day, while the 44 non-transgenic fish grew at 0.224±0.03% per day. This difference is statistically significant.

Figure 7:
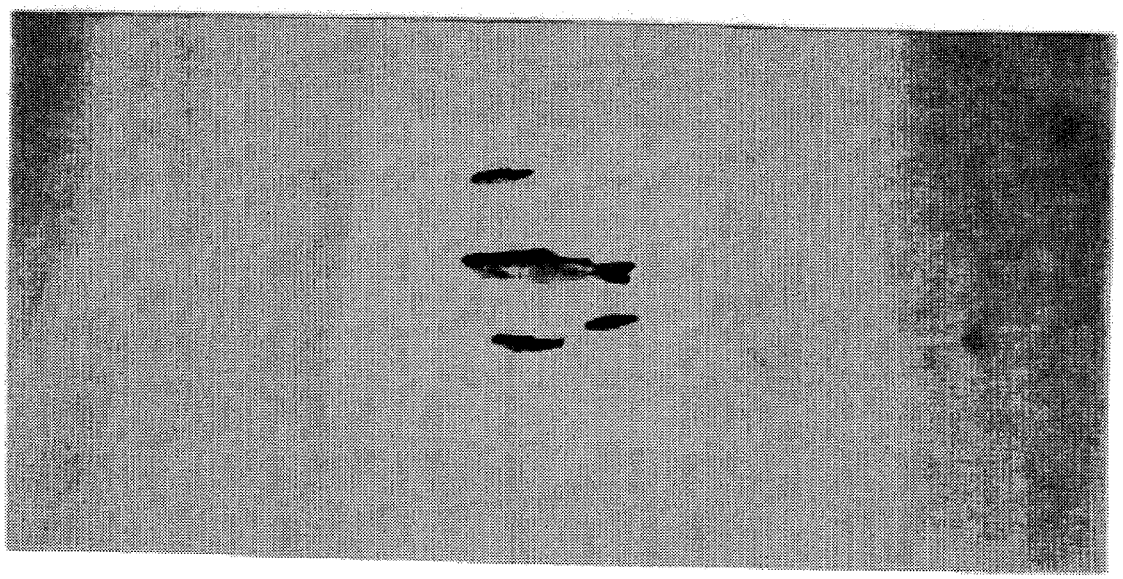
FIG. 7. Transgenic salmon vs nontransgenic salmon.

Smolting is a very complicated transformation process involving many morphological and physiological changes (see review by Hoar 1988). One of the morphological changes is the silvering of smolt. In our studies, the transgenic salmon silvers earlier than the control, suggesting that transgenic salmon smolts earlier (FIG. 7). It has been reported that the fish size and growth rate appear to be the significant factors in controlling the salmon smolting (see review by Hoar 1988), this is supported by our observation that the transgenic salmon smolt earlier than their control. Therefore, the transgenic salmon appears to be a good model for the study of salmon smolting.

Recently, PCR has become a useful tool to analysis the DNA where the source of DNA is limited. PCR has been used in screening for transgenic mouse (Chen and Evans 1990), the blood cell were lysed by SDS and DNA was used directly for PCR. Recently, Henley and Merile (1991) reported the transgene detection in mouse by PCR using unpurified tail DNA. Our data revealed that 1 µl of blood is sufficient for screening of transgenic fish directly by PCR. This protocol has been adopted for the routine analysis in the laboratory for the detection of several thousand samples.

It is appreciated that there are other promoter systems which, in accordance with this invention, work equally in a transgenic gene construct. Other promoter sequences isolated from wolf fish and winter flounder are useful. A sequence comparison of the promoter sequence of wolf fish and OP-3 and OP-5 of Ocean pout is provided in Table IV. In this Table, the (–) beneath a DNA base pair (bp) indicates the same, whereas a different letter indicates a different bp in the sequence comparison of the three promoters.

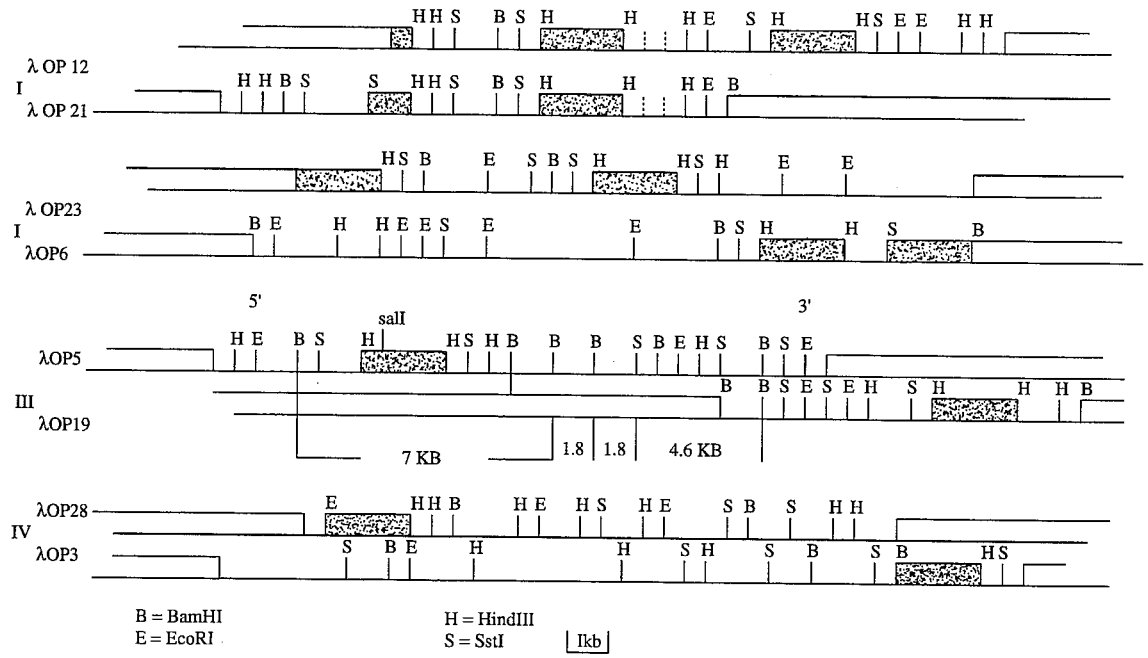

TABLE II

Promotor Analysis of Antifreeze in RTH Cell Line and Japanese Medaka Embryos

TABLE II-continued

Promotor Analysis of Antifreeze in RTH
Cell Line and Japanese Medaka Embryos

| Construct | CAT Activity MADAKA | RTH |
|---|---|---|
| opAF-93 | 132.8 | 100 |
| opAF-77 | 30.0 | 25 |
| opAF-51 | 24.0 | 30 |
| opAF-16 | 0.5 | 3 |
| B. | | |
| woAF-1750 | 24.7 | 16 |
| woAF-313 | 122.8 | 91 |
| woAF-203 | 1.0 | 22 |
| C. | | |
| srAF-2300 | 123.5 | 9 |
| srAF-225 | 33.5 | 9 |
| srAF-51 | 118.5 | 100 |
| srAF-21 | 104.3 | 40 |
| D. | | |
| wfAF-2300 | 60.0 | 7 |
| wfAF-571 | 7.1 | 10 |
| wfAF-181 | 64.8 | 10 |
| wfAF-143 | 5.8 | 10 |
| wfAF-85 | 0.9 | 9 |
| wfAF-66 | 1.4 | 10 |

TABLE IV

```
       Hind III
WO AAGCTTCATGGAAAAGTACAAGCAATTTGCACACATCATTCTGTATTTTTCCAACAGCTT  −264
OP3 --------------------T--------T--------------------T---*A      −246

< a  >< a  >< a  >           Pvu II                RooRV
WO TAATGTCATTGTGTCATTGTGCTATTGGATAGAAGAGACCAGCTGATCTAGACAGTTGAT  −204
OP3 C--------C---A---CA--------------------------------------    −185
```

TABLE IV-continued

```
              Sph I                              <    b    ><
WO  ATCATGATTAACAGCCCCAAACAACAAGTGTGCATGCGTGAGGAGTGATTGGCAGATGTA  -144
OP3 -------------------------------T----------------------*     -127
OP5                          AAGCTTGTGATAGTTTGGACAAAAACAAGTTATACTTTACT  -144
                             Hind III b     >                                                  Mae III
WO  TTGGCAGATGTATGAGAGCAATTACAATTTGACTTAAGGAGGTTTGACACAGTGACCTACT  -84
OP3 **********------******-----------A-------------------------  -84
OP5 TATAAGAATATAAAATTT-C---G-------G-A--------------------------  -84

Hae III                    HpaII
WO  TTCAGG CCAAT AGGAAACGGGATATGCCGGTTAAGTCCTCCCACATACTG TATA TTAGAT  -24
OP3 ------ -----  --------------A-------------------- ---- ------  -24
OP5 ------ -----  -----------------------------------  ---- ------  -24

NIa III             +1 <      c       >
WO  GCAGCACATGAACCTGTCCTGTCAGAAGTCTCAGCTACAGCTTTCACTTCTTTCTCCCCT  +37
OP3 ----------------T-----------------------------G----------    +37
OP5 ---------G--------------------------------GA------A-         +37
                                               Sau3AI

AsaI                            <     c    >
WO  AATTAATTAATTA********CTAATTAATTAAGTCTCAGCCACAGCCATG  +80
OP3 -------------********----------------------------- +80
OP5 -------------ATTAATTAT---------------------------- +88
```

---

SEQUENCE LISTING ( 1 ) GENERAL INFORMATION:

( i i i ) NUMBER OF SEQUENCES: 6

( 2 ) INFORMATION FOR SEQ ID NO:5:

( i ) SEQUENCE CHARACTERISTICS:
        ( A ) LENGTH: 1904 base pairs
        ( B ) TYPE: nucleic acid
        ( C ) STRANDEDNESS: single
        ( D ) TOPOLOGY: linear ( i i ) MOLECULE TYPE: DNA (genomic)

( i x ) FEATURE:
        ( A ) NAME/KEY: 5'clip
        ( B ) LOCATION: 1..1904
        ( D ) OTHER INFORMATION: /note="Promoter sequence from
            Ocean Pout antifreeze protein."

( x i ) SEQUENCE DESCRIPTION: SEQ ID NO:5:

```
GGATCCCCCA  GAATGAGCTG  GAACATGTTG  CGGGGAGAGG  GAAGTCTGGG  TCAGCCTGCT    60

TGGCCTGCTG  CCACCGTGAC  CCGACCTCAG  ATAAGCGGAG  GAAAATGGAT  GGATGGATTG   120

AATCACAGAA  TGTTTCTGAA  GACAGATATC  ACCTTCGCTT  CAAAGAGGTG  CGCACCTGGG   180

CAGGCACCCA  CACAGCACA   CAAATGGCAT  ATGAATCAAC  CAAGAAGACG  GTTGGAACTG   240

GTCAAAACCT  TCACTATACC  ATGTGTGACA  GTTGTTTGTC  ACAGTGTATA  AAAGACAGGG   300

ACTTAGAGAC  AGAGCTCTGA  GCAGCTATGA  GATTGTAGTT  TGGCCAGGAT  GCGCTTAAGA   360

CCTTTGTGAT  GAAAAGTTAT  CAAATTCGTG  AGTTTTCATG  GAAGAACCTT  GACGTGGCGT   420

GGTGGCCATT  TTGCGTCATT  CGGCATGGAA  AAGGAAGTCG  TTATAACTCC  CAGGTACATT   480

ATCTTATCTA  CACAAAATGT  CTAATGCATG  ATACTACTTA  AAGCCTGAGC  ATATTTCAAG   540

GCCAGCACTT  TTCAATAACT  CATAGGCCAC  CTGCTGGCAA  AAGGAAATGC  CACATTTTAT   600

ACTTTTATTT  ACTCCTAGAC  AGTTGACCTG  ATCAGTCTCA  AATTTGGTAA  GGATAGCCTT   660

AAGACAATGA  AGATGCTTCA  TCAGGAATAT  TGTGAGTTGT  CGTTGAACGT  TGTTGCCGTG   720
```

| | | | | | | |
|---|---|---|---|---|---|---|
| GCAACGCATC | ATTCGCCATG | AAAAAGAAGC | TGATGGTTCA | GTGGCTTGGG | ATGCTCAAAA | 780 |
| AGTCATGGAA | CTTTGTACAT | GTGTCATAAT | TGATGGGAAG | TTGTATGGGT | TTTTGGCTTG | 840 |
| CTTGTTATAA | ATTGTCTCCA | TAGCGCCCCC | TACAATATTT | CAAAGAGCA | GCCCCAGTGC | 900 |
| TACGTACATG | TATGAAACTT | AGTAGCCAGA | TGTACCATAT | AGAGACTTAC | AAAAAGGTAT | 960 |
| CTTGGCCATG | CTCTCAACCG | TACTGGAAGT | CGGCCATTTT | GATTTTTGCA | TAATTTTTCA | 1020 |
| ATAGATTTTT | GCACATTTGT | AATCGCTATA | CTTTAACGAA | CTCCTCCAAG | GAACTTTGTC | 1080 |
| TAATCAATTT | CAAATTTTGT | CAGTACAATC | TCAGTACTAC | AGTACCAAAT | CTACAGTTCT | 1140 |
| GCATCTCGTA | GCTGCTCAGA | GGTCTGTCTC | TAAGTCCCTG | TCTTTTATAC | ACTGTGACAA | 1200 |
| ACAACTGTCA | CACATGGTAT | AGTGAAGGTT | TTGACCAGTT | CCAACCGTCT | TGTTGGTTGA | 1260 |
| TTCATATGCC | ATTCGTGTGG | CTGTGTGGGT | GCCTACCCAG | ATGCGCACCT | CTTTGAAGCG | 1320 |
| AATGTGATAT | CTGTCTTCAT | AAACATTCTG | TTATTAGCAA | GTTCATATGA | GAATGAAGGC | 1380 |
| TGTATGCAAA | CAGGTGCACA | GTCTGTTTCT | AAGCATCATG | GAAAAGTACA | AGCAATTTGC | 1440 |
| ACAAATCATT | CTGTATTTTT | CCAATAGCTA | ACAATGTCAC | CGGGACATTG | TGCTATTGGA | 1500 |
| TAGAAGAGAC | CAGCTGATCT | AGACAGTTGA | TATCATGATC | AACAGCCCCA | AACAACAAGT | 1560 |
| GTGCATGCGC | GAGGAGTGAT | TGGCAGATGT | ATGAGAACTA | AACCACTGAC | TGAACTTGCA | 1620 |
| CTAGAGGCAT | CTATTTTGTC | TTTTCTCATA | TGATGTTGGG | ATGGCACATG | GGAGTTTTTC | 1680 |
| CCCTGTCTCA | GCTTGCTTTT | TACCCCAAAT | ATTGTATATC | TATTAGAACC | GTTGTCACAG | 1740 |
| GGTTCAAATT | AACGTTTTAG | TTTAGTTTTG | ATCATGATAT | ACACATTTTA | TCCGTAAAGC | 1800 |
| ATGTGCATAT | ACAGTAAGGG | CTTGTTATTC | GACAGCAAGA | AGAAGAGGAT | ATGTGTGCAG | 1860 |
| GCAGTCAGCT | AATGCATGGA | TCACAAGTTA | TAGAATGCAA | GCTT | | 1904 |

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GTCAGAAGTC TCAGCTACAG C                                                   21

( 2 ) INFORMATION FOR SEQ ID NO:7:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:7:

ATCTCAACAG TCTCCACAGG T                                                   21

( 2 ) INFORMATION FOR SEQ ID NO:8:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:8:

TCTGCTGATG CCAGTCTTAC T                                                            2 1

( 2 ) INFORMATION FOR SEQ ID NO:9:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:9:

ACAGAAGTCC AGCAGGAATA T                                                            2 1

( 2 ) INFORMATION FOR SEQ ID NO:10:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:10:

GAAATGTTC AATGACT                                                                  1 7

We claim:

1. A method of increasing the growth rate of a salmonid fish comprising the steps of:
   a) introducing into the germ line of a salmonid fish a gene encoding a salmonid growth hormone operably linked to a type 3 antifreeze protein promoter; and,
   b) culturing said salmonid fish under conditions wherein said salmonid fish expresses said growth hormone gene at levels which increase the rate of its growth at least four times that of a salmonid fish lacking said growth hormone gene operably linked to said antifreeze protein promoter.

2. A method of claim 1 wherein said antifreeze protein promoter is from ocean pout and said growth hormone gene is the endogenous growth hormone gene.

3. A method of claim 1 wherein said salmonid fish is selected from the group consisting of Atlantic salmon and Chinook salmon.

4. A transgenic salmonid fish containing in its germline a salmonid growth hormone gene operably linked to a type 3 antifreeze protein promoter wherein said salmonid fish expresses said growth hormone gene at levels which increase the rate of its growth at least four times that of a salmonid fish lacking said growth hormone gene operably linked to said antifreeze protein promoter.

5. A transgenic salmonid fish of claim 4 wherein said antifreeze protein promoter is from ocean pout and said growth hormone gene is the endogenous hormone gene.

6. A transgenic salmonid fish of claim 4 wherein said salmonid fish is selected from the group consisting of Atlantic salmon and Chinook salmon.

7. A transgenic salmonid fish of claim 5 wherein said salmonid fish is Atlantic salmon.

\* \* \* \* \*